United States Patent
Stocker et al.

(10) Patent No.: US 6,426,192 B1
(45) Date of Patent: Jul. 30, 2002

(54) METHOD FOR THE FUNCTIONAL DETECTION OF DISORDERS IN THE PROTEIN C SYSTEM

(75) Inventors: Kurt Stocker, Obergestein; Patrizia Gempeler-Messina; Christian Müller, both of Reinach, all of (CH)

(73) Assignee: Pentapharm AG (CH)

( * ) Notice: Subject to any disclaimer, the term of this patent is extended or adjusted under 35 U.S.C. 154(b) by 0 days.

(21) Appl. No.: 09/403,805

(22) PCT Filed: Apr. 24, 1998

(86) PCT No.: PCT/CH98/00168
§ 371 (c)(1),
(2), (4) Date: Jan. 19, 2000

(87) PCT Pub. No.: WO98/49562
PCT Pub. Date: Nov. 5, 1998

(30) Foreign Application Priority Data

| Apr. 25, 1997 | (CH) | 974/97 |
|---|---|---|
| Sep. 3, 1997 | (CH) | 2062/97 |

(51) Int. Cl.$^7$ .............................. C12Q 1/56; C12Q 1/37
(52) U.S. Cl. ............................ 435/13; 435/23; 435/975
(58) Field of Search .............................. 435/13, 23, 975

(56) References Cited

U.S. PATENT DOCUMENTS

| 5,443,960 A | * | 8/1995 | Dahlback | |
| 5,726,028 A | * | 3/1998 | Kraus | 435/13 |
| 6,090,570 A | * | 7/2000 | Kraus | 435/13 |

FOREIGN PATENT DOCUMENTS

| EP | 0 711 838 A | 5/1996 |
| WO | WO 96 04560 A | 2/1996 |
| WO | WO 96 15457 A | 5/1999 |

* cited by examiner

*Primary Examiner*—Ralph Gitomer
*Assistant Examiner*—Mahreen Chaudhry
(74) *Attorney, Agent, or Firm*—Pennie & Edmonds LLP

(57) ABSTRACT

The method relates to a method for detecting disorders in the protein C system, and in particular for determining the activated blood coagulation factor V with increased stability with respect to decomposition by activated protein C.

26 Claims, 2 Drawing Sheets

Representation of the sensitivity ratio for the determination of APC resistance

METHOD FOR THE FUNCTIONAL DETECTION OF DISORDERS IN THE PROTEIN C SYSTEM

The present invention relates to a method for the sensitive and functional detection of disorders in the protein C system (protein C, protein S, FV) and in particular for the determination of the activated blood coagulation factor V (FVa) with increased stability in respect of the decomposition by activated protein C (APC).

Hemostasis after vascular injuries results from an interaction between tissue, blood cells (blood platelets) and proteins of the blood liquid (plasma clotting factors, calcium ions). This interaction first leads to the formation of a hemostatic platelet plug (primary hemostasis) and finally to its consolidation by coagulation, i.e. by forming a network of insoluble fibrin. The physiological calcium content in blood of 60–70 mg per liter is essential for the optimal progress of the blood coagulation reactions. The fibrinolytic system is responsible for the enzymatic decomposition of fibrin clots during wound healing and recanalization of closed vessels. These interfering systems are modulated by activators and inhibitors and are present in the healthy organism in a labile balance. Disturbances of this balance may lead on the one hand to increased bleeding tendency and on the other hand to thrombosis proneness. Hemostatic disorders cause or accompany many diseases and therapies, in which cases the balance may be disturbed either in favour of bleeding or of thrombosis.

Figure 1:
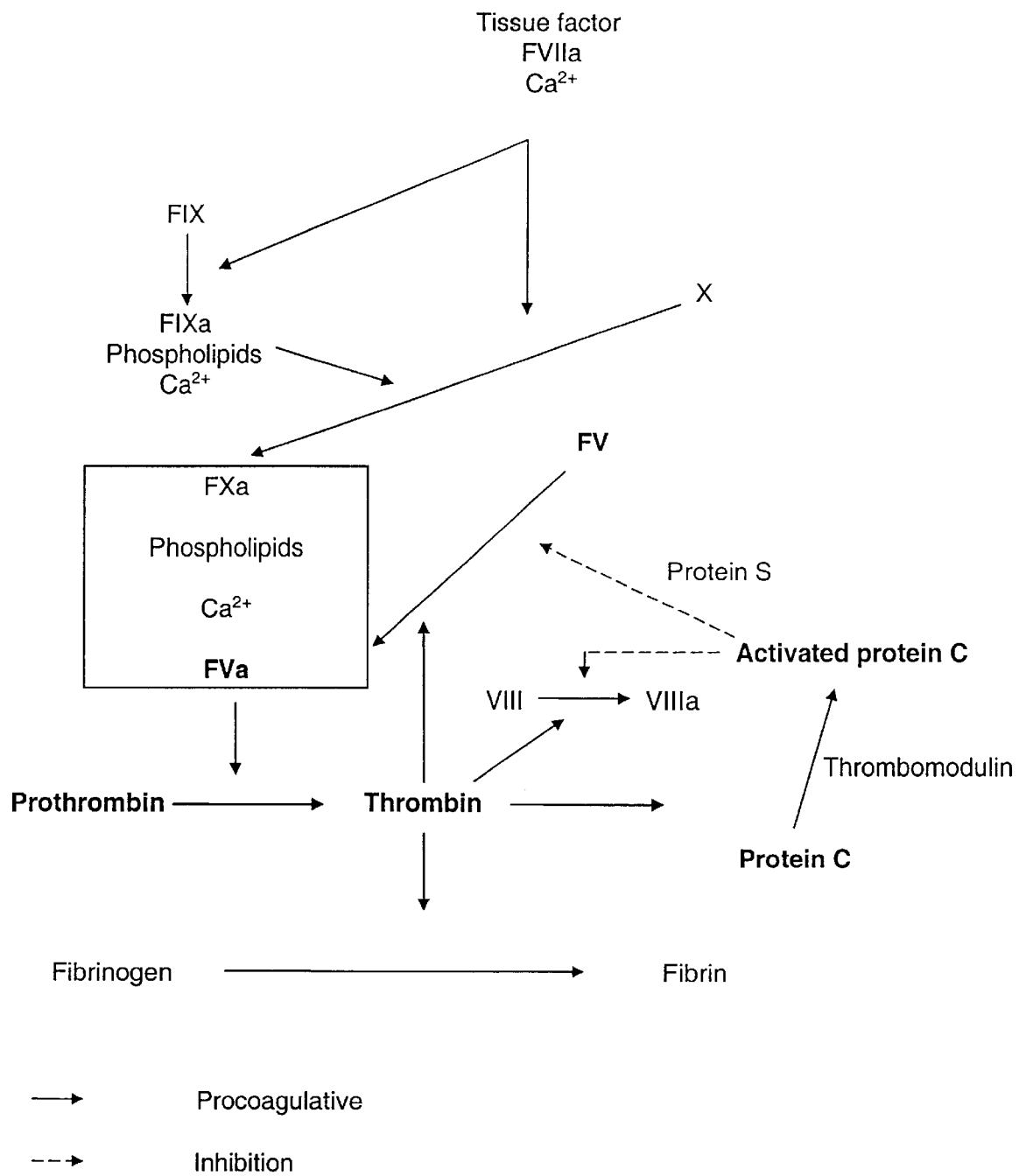

The section of the blood coagulation cascade represented in FIG. 1 is of particular importance for the present invention. A detailed report on the reaction cascade leading to blood coagulation can be found in H. R. Roberts, Overview of the Coagulation Reactions, in: K. A. High and H. R. Roberts (eds.) Molecular Basis of Thrombosis and Hemostasis, pp. 35–50, Marcel Dekker: New York, Basel, Hong Kong (1995).

After injury of the vessel wall, blood comes into contact with tissue cells that release on their surface a glycoprotein of 50,000 Dalton which, as the so-called thromboplastin or tissue factor (TF), activates the blood clotting system via the exogenous pathway. Blood platelets adhering to tissue structures release phospholipids which activate the intrinsic blood coagulation system. TF forms with factor (F) VII present in plasma a complex that activates the zymogens FX and FIX to the serine proteases FXa and FIXa. Via the endogenous pathway, FIXa together with its cofactor FVIIIa also forms an efficient activator for FX in the presence of calcium ions and phospholipids. FXa forms with FVa, calcium ions and phospholipids a complex (prothrombinase complex) which converts the zymogen prothrombin into catalytically active thrombin. The enzyme thrombin converts fibrinogen by limited proteolysis into fibrin monomer which spontaneously polymerizes into fibrin.

The factors Va and VIIIa are non-enzymatic plasma proteins that strongly accelerate the activation of FX and prothrombin, respectively, by FIX and FXa, respectively. The catalytic efficacy of the cofactor, FVa, on the prothrombin activation is shown in Table 1. It can be seen that the activation of prothrombin by FXa, phospholipids and calcium ions is accelerated about 250 times alone by the presence of FVa.

The presence of calcium ions and phospholipids is a condition sine qua non for most reactions of the blood coagulation cascade. Removal of calcium ions by complexation, precipitation or ion exchange totally inhibits the clotting capacity of blood. This property is generally used to obtain blood plasma for analytical or therapeutic purposes by mixing freshly collected blood with sodium citrate for the complexation of calcium ions, centrifuging and decanting the supernatant, unclottable blood liquid from the sedimented cells. The coagulability of citrate plasma is restaured by addition of a physiological quantity of a calcium salt, by so-called recalcification.

TABLE 1

| Catalytic efficacy of the prothrombinase complex Prothrombin activation by the prothrombinase complex | |
| --- | --- |
| Xa | 1 |
| Xa, $Ca^{2+}$ | 1.7 |
| Xa, $Ca^{2+}$, PL, | $8.3 \times 10^3$ |
| Xa, $Ca^{2+}$, PL, Va | $2.0 \times 10^6$ |

The anticoagulant protein C system prevents an uncontrolled migration of activated blood clotting factors from the site of the vascular injury and hemostasis. As in the plasmatic coagulation system, a cell-bound receptor, thrombomodulin (TM), and a non-enzymatic cofactor, protein S, as well as the secondary components phospholipids and calcium ions participate in the activation of the protein C system. Thrombin escaping from the site of hemostasis binds to TM, loses thereby its fibrinogen-coagulant properties and becomes the specific activator for the zymogen protein C. Activated protein C (APC) is a serine proteinase which, potentiated by protein S, splits off and inactivates the clotting factors FVa and FVIIIa. By inactivation of these cofactors, the coagulation process is strongly slowed down: according to Table 1, a 250-fold delay takes place alone by the inactivation of FVa. For a topical description of the protein C system, see K. Suzuki, Protein C: in: K. A. High and H. R. Roberts (eds.) Molecular Basis of Thrombosis and Hemostasis, pp. 393–424, Marcel Dekker: New York, Basel, Hong Kong (1995).

The biological significance of the protein C system has been evidenced in 1993 by B. Dahlback who observed that in patients with thrombosis tendency, unlike in healthy subjects, the activated partial thromboplastin time (APTT, a diagnostic function control for the endogenous coagulation system) is not prolonged after addition of activated protein C. He defined his observations as "resistance against activated protein C" (APC resistance). This resistance is in 97% of the cases due to a point mutation in the factor V gene. This genetically inherited defect can be found in about 5% of the normal population and in at least 20% of young patients with first unexplainable or recurrent thromboembolisms. In the presence of the mutation, the activated clotting factor V can no more be split and thus inactivated. Consequences of the deficiency of this particularly important anticoagulant component of the blood coagulation system may be coronary heart diseases, venous thromboses or thromboembolisms. Consequently, heterozygous defect carriers present a 5–10 times greater thrombosis risk than normal persons and homozygous defect carriers an even 50 to 100 times higher risk.

Other hereditary or acquired deficiencies or defects in the protein C system (qualitative or quantitative protein C or protein S deficiency) are also associated with higher thrombosis tendency.

The congenital or acquired APC resistance can be detected by a functional test or by the direct detection of the mutation on the DNA level (genotype).

The functional detection can be performed according to Dahlback by an APTT variant (PCT/SE92/00310; WO 93710261) in which the coagulation of a platelet-free plasma sample is once triggered off once by calcium chloride without addition of activated protein C (APC) and once by calcium chloride with addition of APC. The thrombin quantity resulting in the test mixture is determined either by the conversion of the natural substrate fibrinogen into a clot (clotting time) or photometrically by the release of a chromophore from a chromogenic substrate. The existence of the factor V mutation can be noted by the fact that the clotting time is only weakly prolonged by APC, while APC strongly prolongs the APTT of normal plasma. Dividing the clotting time of the sample with APC by the clotting time of the sample without APC gives a ratio of diagnostic significance. A ratio of more than 2.0 is found in healthy subjects, a ratio between 1.3 and 2.0 in heterozygous and a ratio below 1.3 in homozygous defect carriers. However, as this test system bases on the activation of coagulation in the presence of calcium ions, quantitative and qualitative abnormalities on calcium-dependent plasma Table 1. Catalytic efficacy of the prothrombinase complex clotting factors (FII, VII, VIII, IX, X) can falsify the result. Deficiency or dysfunction of protein S can give erroneously positive values and the presence of antiphospholipid antibodies (lupus anticogulants) erroneously negative values. The presence of platelets in a carelessly prepared plasma sample can influence the result and finally a therapy with oral anticoagulants or heparin may influence the test result of a plasma sample.

Following Dahlbäck's work, researchers focused on improvements or modifications of the original test system. So, for a more specific functional determination of APC resistance for example, it is recommended to mix the sample to test with FV-deficient plasma in the ratio 20:80 before use in the test method (Behringwerke EP 0711838 A1). The used FV-deficient plasma should contain a normal factor VIII concentration, as too high or too low FVIII concentrations in the patient sample would falsify the results. This method allows to reduce disturbances due to abnormalities in calcium-dependent plasma clotting factors (Witt I., Kraus M. APC-Resistenz: Klinik, Pathophysiologie und Diagnostik. Hämostaseologie, 1996; 16:60–67).

The disturbing influence of heparin can be reduced by addition of a heparin antagonist, e.g. hexadimethrine bromide (polybrene), whereby the false clotting time is however only corrected in the presence of APC. The APTT without APC addition remains prolonged, so that in this case the APC ratio cannot be used for evaluation. Moreover, the presence of lupus anticoagulants, which also causes an APTT prolongation, is no more noticeable. In this case, an additional test on lupus anticoagulants is thus required. Calculation of the APC ratio must not be undertaken in the case of an abnormal APTT exceeding 50%.

Exner (PCT/AU95/00474; WO 96/04560) describes modifications of Dahlbäck's patent. Here the endogenous factors V and X are activated by the use of snake venoms, whereby an increased sensitivity should be reached. As this test principle also requires the presence of calcium ions, it is neither possible with this test variant to identify all APC-resistant plasmas and distinguish them from normal ones.

For the above mentioned reasons, the prior-art functional tests available, working in the recalcified reaction mixture, don't yet allow to diagnose an APC resistance with 100% certainty. There are always borderline plasma samples, i.e. the differentiation between normal plasmas and plasmas from patients with heterozygously acquired or hereditary FV mutation and the differentiation between heterozygous and homozygous mutation carriers is often impossible. Consequently, a definite determination is only possible with the complex, cost- and time-consuming genome analysis through PCR (polymerase chain reaction).

It has now been surprisingly found that the FV dependence of prothrombin activators from defined snake venoms, which are described in the literature as calcium-, phospholipid- and FV-dependent, is higher in the absence than in the presence of calcium ions. Moreover, it has been found that the stimulating cofactor effect of factor Va is particularly obvious when, instead of calcium ions, even a calcium-complexing agent, e.g. the chelating agent ethylenediaminetetraacetic acid (EDTA), is added to the test mixture (Example 1). It has been finally found that the said snake venom activator is extraordinarily appropriate for the specific and diagnostic detection of acquired or hereditary APC resistance in the absence of calcium ions in the test mixture.

The method basically comprises incubating a plasma sample with a protein C activator and/or APC, triggering the coagulation by adding a calcium-independent, but FV-dependent prothrombin activator, however without addition of calcium ions, measuring the clotting time and comparing the latter to the clotting time of a reference plasma. The clotting time is prolonged in normal plasma, but not in plasma with APC resistance, so that comparing the clotting time of the plasma sample with the clotting time of the reference plasma easily allows to conclude the presence or absence of an APG resistance.

The reference plasma without APC resistance can be composed of many normal plasmas, a mixture of normal and/or heterozygous and/or homozygous plasmas or a unique plasma (=normal plasma). Comparison of the clotting times of the plasma sample with those of the reference plasma can be performed with as well as without addition of a protein C activator or APC, respectively, to the reference plasma.

In addition, part of the plasma sample to investigate may be used as the reference plasma.

The devices for measuring the clotting time can be adjusted with a reference plasma in such a way that the clotting time of the reference plasma amounts to e.g. 80–140 seconds. Thereby, the ratio between mutated and normal factor V in the reference plasma can be comprised e.g. between 20:80 and 80:20.

The adjustment of the devices with reference plasmas can be carried out e.g. once monthly or in parallel to the measurements of the plasma samples.

However, it is not necessary to adjust the devices for the measurement of the clotting time. It is generally sufficient to measure the clotting time of a plasma sample and compare it to the pragmatical values of reference plasmas, added e.g. to the test kits as tables. From the compared values, it can be finally concluded on homozygous, heterozygous or normal blood plasma, what—compared to the prior art-required measurements-represents a considerable simplification.

Should part of the plasma sample to investigate be simultaneously used as the reference plasma, it is possible to a) incubate part of a plasma sample with a protein C activator and/or APC, trigger off the coagulation by addition of a calcium-independent prothrombin activator without addition of calcium ions to the test system, b) trigger off the coagulation in another part of the plasma sample without addition of a protein C activator and/or APC by addition of a calcium-independent prothrombin activator without addition of calcium ions to the test system and c) measure the clotting time and prove the disturbance in the protein C system from the comparison of both clotting times or from the value of the quotient of both clotting times from parts of the respective sample as previously mentioned under a) and b).

The sensitivity of the method is considerably increased by addition of a calcium-complexing agent and its specificity for mutated FV can be increased by dilution of the plasma sample with FV-free plasma.

Performing one test with and one test without APC addition and calculating a ratio is not necessary if the method of the present invention is carried out under standard conditions referring to reagents, additives and devices. In this case, the clotting time or the substrate splitting, respectively, allows to directly determine the FV quality in the plasma sample.

The advantage of this method lies in the fact that the $Ca^{2+}$-dependent, competitive or disturbing actions leading to prothrombin activation, increased or reduced factor VIII concentration, specific inhibitory antibodies against defined plasma components, e.g. lupus anticoagulant, presence of platelets, plasmas from orally anticoagulated and heparinized patients are repressed by the absence of calcium ions.

In addition, a particular advantage of the method of the present invention lies in the specific, functional detection of structural modifications of FV and in particular of the frequent $FV:Q^{506}$ mutation (FV Leiden). This part can be obtained in the normal case by determination of the plasma clotting time in the presence of APC (examples 3 and 5) as well as in the presence of an adequate protein C activator (examples 2 and 4) during prothrombin activation in the absence of calcium ions and possibly presence of chelating agents such as EDTA and comparison of this plasma clotting time with that of a reference plasma. As appropriate protein C activator, e.g. Protac®, a product commercially available from the firm Pentapharm Ltd. (Kurt F. Stocker and Lars G. Svendsen, EP 0 203 509 B1), can be used. The specificity of both methods (APC and protein C activator, respectively) is so high that homozygous carriers of APC-resistant factor V, heterozygous carriers of APC-resistant FV and normal populations can be distinguished in very good approximation. Moreover, the obtained values also allow to determine whether heterozygous carriers contain more or less APC-resistant FV.

The method of the present invention can be easily adapted to different techniques of blood coagulation analysis. Thus, chromogenic, fluorogenic or amperogenic substrates or other state-of-the-art methods of determination can also be used for determining the values to define. Accordingly, the composition of the test mixture can be adapted to the methodical and technical requirements by modifying the nature or quantity of chelating agents, by specifically adjusting the pH value or by adding defined inhibitors of the clotting system (incl. PC system).

Besides the commercial Protac®, protein C activators or possibly purified fractions from venoms of the snake Agkistrodon contortrix and its subspecies, Agkistrodon piscivorus and its subspecies, Agkistrodon bilineatus and its subspecies or Agkistrodon halys and its subspecies can be basically used as protein C activators.

As this method basically allows to determine not only factor V but also protein C or protein S defects, it can be advantageous to add corresponding deficient plasmas, e.g. FV, protein C or protein S-deficient plasma. The test procedure doesn't react sensitively to the present quantities of deficient plasma, allowing the addition of small quantities of e.g. 1% up to large quantities of e.g. 99% deficient plasma without considerably modifying the determined values. $\geq 50\%$ deficient plasmas are advantageously used.

The addition of phospholipids is not required for carrying out the method of the present invention. As, however, plasma contains various traces of phospholipids—depending on the course of its preparation—, a phospholipid addition could limit the range of variation of the test results.

As calcium-independent prothrombin activators, FV-dependent snake venom enzymes in the form of crude venoms as well as purified venom fractions can be used in the present invention. Prothrombin activators are calcium-independent if they are capable of fully exerting their function according to the present invention also without addition of calcium. For their practical use, the prothrombin activator preparations may be provided with stabilizing additives known per se. Appropriate snake venoms or purified snake venom fractions for the preparation of prothrombin activator preparations of the present invention are venoms with a dominant FV-dependent prothrombin-activating effect, which also develops without calcium addition. The snake venoms preferentially used in the present invention are from the elapid species Notechis, Tropidechis, Cryptophys, Hoplocephalus and Pseudechis, such as Notechis scutatus scutatus, Notechis ater niger, Notechis ater humphreysi, Notechis ater serventyi, Notechis flinders, Notechis occidentalis, Tropidechis carinatus, Cryptophis nigrescens, Hoplocephalus stephensii and Pseudechis porphyriacus (Example 6). Besides prothrombin activators from snake venom, activators produced from microorganisms with a natural or recombinant genome may basically also be used.

The chelating agent preferred in the present invention due to its wide distribution is EDTA, but examination of different $Ca^{2+}$-chelating agents and calcium-precipitating agents has shown that also other substances structurally different from EDTA, such as citrate or oxalate, may be applied too (Example 7). Among other chelating agents, EGTA (ethylenebis-(oxyethylenenitrilo)-tetraacetic acid), desferoxamine, tetracycline, BAPTA (1,2-bis-(2-aminophenoxy)-ethane-N,N,N',N' tetraacetic acid) and their salts and quin-2 (2-[(2-amino-5-methylphenoxy)-methyl]-6-methoxy-8-aminoquinoline-N,N,N',N'-tetraacetic acid tetrapotassium salt can also be cited. Also other methods can be applied to remove the excess of calcium, e.g. precipitations with sulfate or carbonate, adsorption or processes which exert the EDTA effect on the FV-dependent prothrombin activators.

For the detection of the FV-dependent, APC-sensitive prothrombin activation, the determination of the plasma clotting time can be carried out manually or automatically, mechanically, electromagnetically or photometrically. In a test mixture of the present invention, generated thrombin can also be determined photometrically, fluorimetrically or amperometrically by using appropriate synthetic, chromogenic respectively fluorogenic or amperogenic substrates (Example 8). For an overview on synthetic substrates in hemostaseology, see Witt I., Test systems with synthetic peptide substrates in haemostaseology, Eur. J. Clin. Chem. Clin. Biochem., 1991, 29: 355–374. An adequate chromogenic substrate is, e.g., Tos-Gly-Pro-Arg-pNA-AcOH (Pefachrome® TH) commercially available from the firm Pentapharm Ltd.

According to the present invention, disturbing influences due to heparinized plasmas can be avoided with a heparin antagonist, such as polybrene, protamine salts or heparin-splitting enzymes. With but also without heparin antagonists, it is—contrary to prior art—possible to clearly distinguish between homozygous FV defect, heterozygous FV defect and normal plasmas (Example 9).

The incubation phase in the method of the present invention can be considerably shortened by adding a factor V activator to the test mixture. As factor V activator, e.g.

RVV-V from Vipera russelli or factor V activators from venoms of the snakes Bothrops atrox, Bothrops jararaca, Naja n. oxiana, Echis carinatus, Echis multisquamatus, Vipera ursini, Vipera lebetina, Haemachatus haemachatus, Naja m. mossambica, Naja nivea, Naja nigricollis, Naja h. haje, Naja n. kaouthia, Naja melanoleuca, Pseudechis australis, Pseudonaja t. textilis, Notechis ater, Oxyuranus scutellatus or from the caterpillar Lonomia achelous can be used.

The determination of the APC resistance after collecting and preparation and stabilization of the sample according to the conditions is preferentially carried out in two steps that can nearly not be divided in practice. The two steps may be designed as incubation phase and prothrombin activation phase. Adequate samples that for are, e.g., citrate-stabilized plasma samples. However, stabilizers such as oxalate or EDTA can also be used. The activation of FV from the sample, which can be reached by methods known per se e.g. with RVV-V (from Vipera russelli) occurs during the incubation phase, preferentially in the presence of FV-deficient plasma. This activation reaction with or without APC or a protein C activator belongs to the incubation phase, the required reagents being added with preference at the beginning of the incubation phase. The prothrombin activation phase begins with the addition of the FV-dependent snake venom or the corresponding purified fraction of snake venom, respectively. Adding a chelating agent (e.g. EDTA) to the sample may increase the specificity. Such a chelating agent is typically but not absolutely necessarily added together with the FV-dependent snake venom enzyme.

It has to be noted that the method of the present invention does neither exclude variations with overlapping, step-wise or even continuous addition of individual or several of the cited components. The duration of the incubation phase depends a.o. on the problem and on the nature of the used activation of the APC system. It typically ranges from 1 to 40 minutes, preferentially below 30 minutes.

Kits of the present invention which can be used for the detection of defects in the protein C system, contain APC or protein C activators, such as Protac®, a prothrombin activator and possibly a factor V activator, such as RVV-V. Moreover, phospholipids, factor V-deficient plasma, a Ca complexing agent, such as EDTA, and—depending on the method of detection applied—one or several reference plasmas, and a heparin antagonist can be added to these kits.

In the following the invention is explained in more details by means of examples.

The following abbreviations are used:

APC: activated protein C

RVV-V: FV activator from Vipera russelli

Protac®: Protein C activator from Agkistrodon contortrix contortrix

The way of stabilization of the used plasma samples of the test persons has no importance as representative results are not only obtained with citrate-stabilized samples. The plasma samples were all examined on APC resistance through direct detection of mutation on the DNA level.

EXAMPLE 1

FV Dependence of the Prothrombin Activator from Notechis Scutatus Scutatus Venom The clotting time was determined by means of a coagulometer KC4 (Amelung, Lemgo, Germany). 40 μl of FV-deficient plasma, 10 μl of plasma sample (+FV) or 50 μl of FV-deficient plasma (−FV) were incubated for 1 minute at 37° C. with 50 μl of 50 mM Hepes, pH 7.5. Clotting was triggered off by the addition of 50 μl of 5 μg/ml prothrombin activator from Notechis scutatus scutatus venom in 25 mM $CaCl_2$, 5 μg/ml prothrombin activator without additives or in 10–40 mM EDTA (Table 2). All the reagents were dissolved in 50 mM Hepes, pH 7.5. The clotting time is determined in the presence and absence of FV. A ratio is made from the clotting time with FV and without FV.

The results obtained show how the addition of calcium ions impairs the FV dependence of the test system. The FV dependence of the test system could be considerably strengthened without addition of calcium ions or with addition of EDTA.

TABLE 2

| Additives | Prothrombin activator μg/ml | Clotting time +FV | Clotting time −FV | Ratio +FV/−FV |
|---|---|---|---|---|
| 25 mM $CaCl_2$ | 0.5 | 51.6 | 106.0 | 2.05 |
| without additives | 5 | 46.3 | 141.3 | 3.05 |
| 10 mM EDTA | 5 | 39.2 | 196.3 | 5.00 |
| 20 mM EDTA | 5 | 48.0 | 262.6 | 5.48 |
| 30 mM EDTA | 5 | 59.3 | 334.5 | 5.64 |
| 40 mM EDTA | 5 | 72.0 | 472.3 | 6.56 |

EXAMPLE 2

Determination of the APC Resistance using Protac®

The clotting time was determined with a coagulometer KC4 micro (Amelung, Lemgo, Germany). 40 μl of FV-deficient plasma, 10 μl of plasma sample and 50 μl of 2 U/ml Protac®, 1 U/ml RVV-V and 0.1 mg/ml of cephalin were incubated for 20 minutes at 37° C. Clotting was triggered off by the addition of 50 μl of 5 μg/ml prothrombin activator from Notechis scutatus scutatus venom in 15 mM EDTA. All the reagents were dissolved in 50 mM Hepes, pH 7.5. The clotting time of a plasma sample is compared with the clotting time of a plasma sample from an APC resistance-free plasma pool or with APC resistance-free normal plasmas, respectively. A quotient is made from the two clotting times with Protac® of plasma sample to plasma pool.

The results obtained show that the quotient of the plasma pool over plasmas with heterozygous FV defect to plasmas with homozygous FV defect decreases in such an extent that a distinction is not only possible between normal plasmas and those with FV defects, but also within plasmas between heterozygous and homozygous FV defects.

TABLE 3

| Plasma sample | Clotting time + Protac ® [s] | Clotting time plasma sample/ clotting time plasma pool |
|---|---|---|
| 1. Plasma pool without APC resistance | 97.4 | 1.00 |
| 2. Homozygous FV defect | 44.7 | 0.46 |
| 3. Heterozygous FV defect | 59.9 | 0.62 |
| 4. Heterozygous FV defect | 66.0 | 0.68 |
| 5. Heterozygous FV defect | 61.4 | 0.63 |
| 6. Heterozygous FV defect | 60.3 | 0.62 |
| 7. Heterozygous FV defect | 67.2 | 0.69 |
| 8. Heterozygous FV defect | 61.9 | 0.64 |
| 9. Heterozygous FV defect | 69.7 | 0.72 |

TABLE 3-continued

| Plasma sample | Clotting time + Protac ® [s] | Clotting time plasma sample/ clotting time plasma pool |
|---|---|---|
| 10. Normal | 96.5 | 0.99 |
| 11. Normal | 82.3 | 0.85 |
| 12. Normal | 101.4 | 1.04 |
| 13. Normal | 93.6 | 0.96 |
| 14. Normal | 103.1 | 1.06 |
| 15. Normal | 111.1 | 1.14 |
| 16. Normal | 97.6 | 1.00 |
| 17. Normal | 94.7 | 0.97 |
| 18. Normal | 95.3 | 0.98 |
| 19. Normal | 98.3 | 1.01 |

EXAMPLE 3

Determination of APC Resistance using APC

The clotting time was determined by means of a coagulometer KC4 micro (Amelung, Lemgo, Germany). 40 μl of FV-deficient plasma, 10 μl of plasma sample and 50 μl of 10 μg/ml APC, 10 U/ml RVV-V and 0.1 mg/ml of cephalin were incubated for 8 minutes at 37° C. Clotting was triggered off by the addition of 50 μl of 5 μg/ml prothrombin activator from Notechis scutatus scutatus venom in 15 mM EDTA. All the reagents were dissolved in 50 mM Hepes, pH 7.5. The clotting time of a plasma sample is compared with the clotting time of a plasma sample from an APC resistance-free plasma pool. A ratio is made from the clotting time of the plasma sample with APC and the determined clotting time of the plasmas in the plasma pool (Table 4).

The results obtained show that the exogenous addition of APC prolongs the clotting time of the plasma pool or of the normal plasmas, respectively, while the clotting time of the plasmas with heterozygous and, in particular, with homozygous FV defect is significantly shortened in such an extent that it is not only possible to distinguish healthy plasmas from those with a FV defect, but also heterozygous from homozygous FV defects.

TABLE 4

| Plasma sample | Clotting time + APC [s] | Clotting time plasma sample/ clotting time plasma pool |
|---|---|---|
| 1. Plasma pool without APC resistance | 90.0 | 1.00 |
| 2. Homozygous FV defect | 54.8 | 0.60 |
| 3. Heterozygous FV defect | 59.9 | 0.67 |
| 4. Heterozygous FV defect | 66.0 | 0.73 |
| 5. Heterozygous FV defect | 61.4 | 0.68 |
| 6. Heterozygous FV defect | 58.9 | 0.65 |
| 7. Heterozygous FV defect | 60.3 | 0.67 |
| 8. Heterozygous FV defect | 60.9 | 0.68 |
| 9. Heterozygous FV defect | 67.3 | 0.75 |
| 10. Normal | 96.5 | 1.07 |
| 11. Normal | 77.5 | 0.86 |
| 12. Normal | 79.8 | 0.88 |
| 13. Normal | 82.3 | 0.91 |
| 14. Normal | 101.4 | 1.13 |
| 15. Normal | 76.6 | 0.85 |
| 16. Normal | 93.6 | 1.04 |
| 17. Normal | 103.1 | 1.15 |
| 18. Normal | 79.6 | 0.88 |
| 19. Normal | 111.1 | 1.23 |

EXAMPLE 4

Determination of APC Resistance using Protac®

The clotting time was determined with a coagulometer KC4 (Amelung, Lemgo, Germany). 40 μl of FV-deficient plasma, 10 μl of plasma sample and 50 μl of 2 U/ml Protac®, 1 U/ml RVV-V and 0.1 mg/ml of cephalin were incubated for 20 minutes at 37° C. Clotting was triggered off by the addition of 50 μl of 5 μg/ml prothrombin activator from Notechis scutatus scutatus venom in 25 mM $CaCl_2$ (Table 5 A), without additives (Table 5 B) or in 15 mM EDTA (Table 5 C). All the reagents were dissolved in 50 mM Hepes, pH 7.5. The clotting time is determined in the presence and absence of Protac®. A ratio is made from the clotting time with Protac® and that without Protac®.

Figure 2:
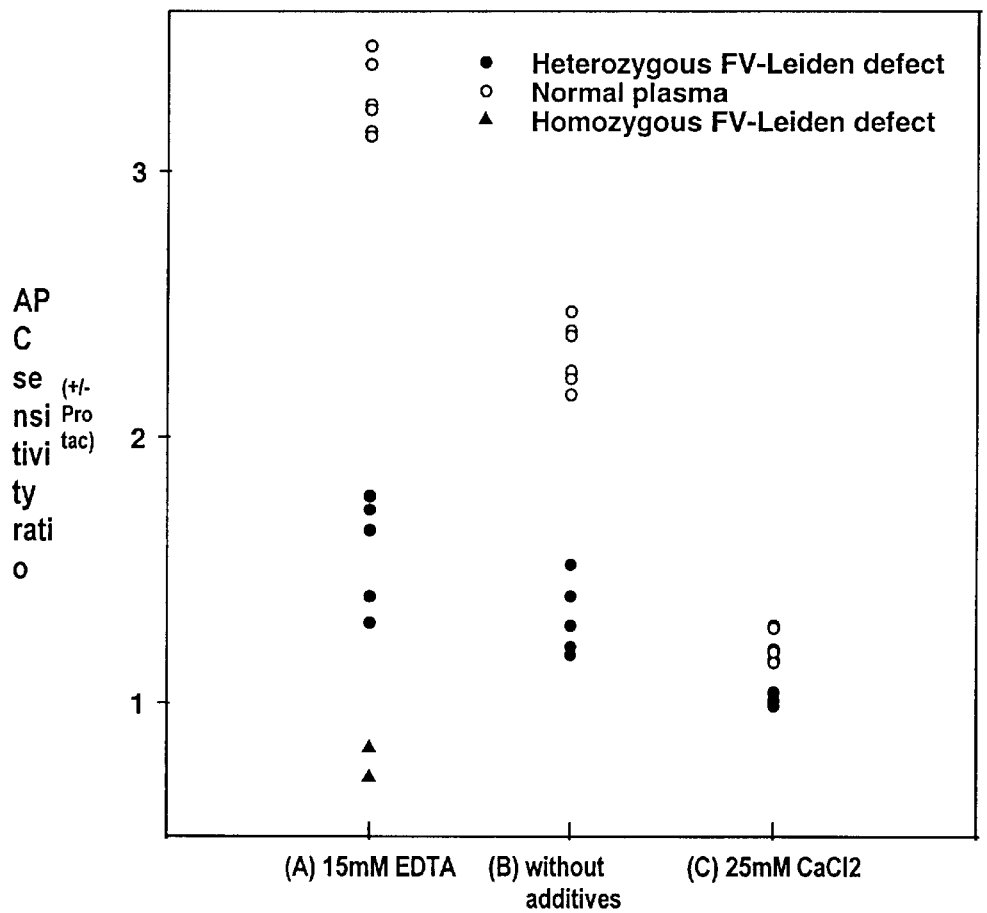

The results obtained show that the ratio is strongly decreased by the addition of calcium ions in normal plasma samples and that it can hardly be distinguished between normal plasma samples and plasma samples with heterozygous FV defect. Surprisingly, the addition of EDTA considerably increases the sensitivity between normal, heterozygous and homozygous plasma samples (FIG. 2).

TABLE 5

| Plasma sample | Clotting time + Protac ® [s] | Clotting time − Protac ® [s] | Ratio +/− Protac ® |
|---|---|---|---|
| A | | | |
| 1. Heterozygous FV defect | 28.3 | 27.9 | 1.01 |
| 2. Heterozygous FV defect | 31.9 | 31.5 | 1.01 |
| 3. Heterozygous FV defect | 26.0 | 26.3 | 0.99 |
| 4. Heterozygous FV defect | 26.1 | 25.9 | 1.01 |
| 5. Heterozygous FV defect | 43.5 | 41.7 | 1.04 |
| 6. Normal | 31.9 | 27.4 | 1.16 |
| 7. Normal | 34.1 | 29.7 | 1.15 |
| 8. Normal | 37.0 | 31.2 | 1.19 |
| 9. Normal | 37.8 | 31.4 | 1.20 |
| 10. Normal | 37.5 | 31.4 | 1.19 |
| 11. Normal | 46.3 | 35.8 | 1.29 |
| 12. Normal | 50.9 | 39.9 | 1.28 |
| B | | | |
| 1. Heterozygous FV defect | 65.5 | 50.9 | 1.29 |
| 2. Heterozygous FV defect | 89.5 | 63.8 | 1.40 |
| 3. Heterozygous FV defect | 55.0 | 46.6 | 1.18 |
| 4. Heterozygous FV defect | 53.5 | 44.2 | 1.21 |
| 5. Heterozygous FV defect | 125.7 | 82.8 | 1.52 |
| 6. Normal | 103.1 | 46.0 | 2.24 |
| 7. Normal | 94.6 | 42.1 | 2.25 |
| 8. Normal | 114.4 | 47.7 | 2.40 |
| 9. Normal | 114.2 | 47.9 | 2.38 |
| 10. Normal | 101.4 | 47.0 | 2.16 |
| 11. Normal | 134.4 | 54.3 | 2.47 |
| 12. Normal | 139.0 | 62.6 | 2.22 |
| C | | | |
| 1. Homozygous FV defect | 44.7 | 53.6 | 0.83 |
| 2. Homozygous FV defect | 57.6 | 79.9 | 0.72 |
| 3. Heterozygous FV defect | 135.6 | 82.1 | 1.65 |
| 4. Heterozygous FV defect | 205.4 | 119.0 | 1.73 |
| 5. Heterozygous FV defect | 101.2 | 77.9 | 1.30 |
| 6. Heterozygous FV defect | 96.9 | 69.1 | 1.40 |
| 7. Heterozygous FV defect | 332.9 | 186.6 | 1.78 |
| 8. Normal | 258.8 | 76.1 | 3.40 |
| 9. Normal | 196.8 | 62.5 | 3.15 |
| 10. Normal | 250.1 | 77.0 | 3.25 |
| 11. Normal | 262.5 | 81.2 | 3.23 |
| 12. Normal | 230.1 | 73.1 | 3.15 |
| 13. Normal | 307.5 | 88.5 | 3.47 |
| 14. Normal | 342.8 | 109.5 | 3.13 |

EXAMPLE 5

Determination of APC Resistance using APC

The clotting time was determined by means of a coagulometer KC4 micro (Amelung, Lemgo, Germany). 40 μl of FV-deficient plasma, 10 μl of plasma sample and 50 μl of 10 μg/ml APC, 10 U/ml RVV-V and 0.1 mg/ml of cephalin were incubated for 8 minutes at 37° C. Clotting was triggered off by the addition of 50 μl of 5 μg/ml prothrombin activator from Notechis scutatus scutatus venom in 15 mM EDTA. All the reagents were dissolved in 50 mM Hepes, pH 7.5. The clotting time is determined in the presence and absence of APC. A ratio is made from the clotting time with APC and that without APC (Table 6).

The results obtained show that the exogenous addition of APC may shorten the incubation without loss of sensitivity in the test system. The normal plasmas can in each case be separated from the heterozygous plasmas. In this example too, no calcium ions are added.

TABLE 6

| Plasma sample | Clotting time + APC [s] | Clotting time − APC [s] | Ratio +/− APC |
|---|---|---|---|
| 1. Normal | 126.0 | 43.0 | 2.93 |
| 2. Heterozygous FV defect | 64.7 | 45.0 | 1.44 |
| 3. Heterozygous FV defect | 68.8 | 47.0 | 1.46 |
| 4. Heterozygous FV defect | 67.3 | 45.3 | 1.49 |

EXAMPLE 6

FV-dependent or Independent Prothrombin Activators from Snake Venoms

The clotting time was determined with a coagulometer KC4 micro (Amelung, Lemgo, Germany). 40 μl of FV-deficient plasma, 10 μl of plasma sample and 50 μl of 2 U/ml Protac®, 1 U/ml RVV-V and 0.1 mg/ml of cephalin were incubated for 20 minutes at 37° C. Clotting was triggered off by the addition of 50 μl of 5–50 μg/ml unpurified snake venom from snakes with FV-dependent or FV-independent prothrombin activators in 15 mM EDTA or 5 μg/ml purified prothrombin activator in 15 mM EDTA. All the reagents were dissolved in 50 mM Hepes, pH 7.5. The clotting time is determined in the presence and absence of Protac®. A ratio is made from the clotting time with Protac® and without Protac® (Table 7).

The results show how purified, FV-dependent prothrombin activators or crude snake venoms with FV-dependent prothrombin activators may be used for the determination of APC resistance. FV-dependent prothrombin activators lead to a ratio with which it is possible to distinguish plasma samples with APC resistance from normal plasma.

TABLE 7

| FV-dependent snake venoms or purified prothrombin activators* | Clotting time + Protac® [s] | Clotting time − Protac® [s] | Ratio +/− Protac® |
|---|---|---|---|
| Normal plasma samples: | | | |
| 1. Notechis ater occidentalis (25 μg/ml) | 166.7 | 70.8 | 2.35 |
| 2. Notechis ater niger (25 μg/ml) | 305.2 | 105.7 | 2.89 |
| 3. Notechis ater humphreysi (25 μg/ml) | 152.6 | 60.5 | 2.52 |
| 4. Notechis ater serventyi (25 μg/ml) | 179.5 | 59.7 | 3.01 |
| 5. Pseudechis porphyriacus (50 μg/ml) | 390.0 | 144.6 | 2.70 |

TABLE 7-continued

| FV-dependent snake venoms or purified prothrombin activators* | Clotting time + Protac® [s] | Clotting time − Protac® [s] | Ratio +/− Protac® |
|---|---|---|---|
| 6. Hoplocephalus stephensii (50 μg/ml) | 208.4 | 78.1 | 2.67 |
| 7. *Tropidechis carinatus (5 μg/ml) | 135.6 | 55.2 | 2.46 |
| Heterozygous FV defect: | | | |
| Notechis ater occidentalis (25 μg/ml) | 122.8 | 80.3 | 1.53 |
| Notechis ater niger (25 μg/ml) | 137.3 | 90.9 | 1.51 |
| Notechis ater humphreysi (25 μg/ml) | 78.5 | 60.3 | 1.30 |
| Notechis ater serventyi (25 μg/ml) | 79.8 | 61.3 | 1.30 |
| Pseudechis porphyriacus (50 μg/ml) | 204.8 | 158.1 | 1.30 |
| Hoplocephalus stephensii (50 μg/ml) | 114.6 | 82.4 | 1.39 |
| *Tropidechis carinatus (5 μg/ml) | 94.9 | 65.4 | 1.45 |
| Normal plasma samples: | | | |
| Akgistrodon rhodostoma (4) (25 μg/ml) | 51.5 | 57.5 | 0.90 |
| Crotalus adamanteus (12) (25 μg/ml) | 70.8 | 77.2 | 0.92 |
| Oxyuranus scutellatus (307) (25 μg/ml) | 21.9 | 21.7 | 1.01 |
| Oxyuranus microlepidotus (337) (25 μg/ml) | 19.0 | 19.3 | 0.98 |
| Pseudonaja textilis | | | |
| (25 μg/ml) | 7.8 | 7.7 | 1.01 |
| (5 μg/ml) | 21.0 | 21.4 | 0.98 |
| Bothrops neuwiedi (25 μg/ml) | 157.8 | 160.9 | 0.98 |
| *Ecarin (5 μg/ml) | >600 | >600 | — |
| *Oxyuranus scutellatus (5 μg/ml) | 21.0 | 21.0 | 1.00 |
| *Textarin® (5 μg/ml) | >600 | >600 | — |
| Heterozygous FV defect: | | | |
| Akgistrodon rhodostoma (25 μg/ml) | 50.8 | 53.5 | 0.95 |
| Crotalus adamanteus (25 μg/ml) | 65.2 | 74.6 | 0.87 |
| Oxyuranus scutellatus (25 μg/ml) | 26.5 | 25.8 | 1.03 |
| Oxyuranus microlepidotus (25 μg/ml) | 18.2 | 19.6 | 0.93 |
| Pseudonaja textilis (5 μg/ml) | 21.2 | 21.6 | 0.98 |
| Bothrops neuwiedi (25 μg/ml) | 155.9 | 154.5 | 1.01 |
| *Ecarin (5 μg/ml) | >600 | >600 | — |
| *Oxyuranus scutellatus (5 μg/ml) | 21.0 | 20.8 | 1.01 |
| *Textarin® (5 μg/ml) | >600 | >600 | — |

EXAMPLE 7

Influence of Different Chelating Agents on the Test System

The clotting time was determined by means of a coagulometer KC4 (Amelung, Lemgo, Germany). 40 μl of FV-deficient plasma, 10 μl of plasma sample and 50 μl of 2 U/ml Protac®, 1 U/ml RVV-V and 0.1 mg/ml of cephalin were incubated for 20 minutes at 37° C. Clotting was triggered off by the addition of 50 μl of 5 μg/ml prothrombin activator from Notechis scutatus scutatus venom in 15 mM EDTA, citrate or oxalate. All the reagents were dissolved in 50 mM Hepes, pH 7.5. The clotting time is determined in the presence and absence of Protac®. A ratio is made from the clotting time with Protac® and without Protac® (Table 8).

The results show that the addition of different chelating agents strengthens the FV dependence.

TABLE 8

| | Clotting time + Protac® [s] | Clotting time − Protac® [s] | Quotient +/− Protac® |
|---|---|---|---|
| 1. 15 mM EDTA | 162.1 | 62.5 | 2.59 |
| 2. 15 mM citrate | 115.4 | 55.8 | 2.07 |

TABLE 8-continued

| | Clotting time + Protac ® [s] | Clotting time − Protac ® [s] | Quotient +/− Protac ® |
|---|---|---|---|
| 3. 15 mM oxalate | 92.8 | 49.1 | 1.89 |
| 4. without additives | 76.4 | 46.3 | 1.65 |

EXAMPLE 8

Determination of APC Resistance using a Chromogenic Substrate

The extinction variation per minute is determined photometrically at 405 nm (Perkin Elmer UV/VIS LAMBDA BIO 10). 40 µl of FV-deficient plasma, 10 µl of plasma sample and 50 µl of 10 µg/ml APC, 10 U/ml of RVV-V and 0.1 mg/ml of cephalin were incubated for 8 minutes at 37° C. In a second step 50 µl of the above activated mixture is added to 750 µl of 50 mM Hepes, pH 7.5, 100 µl of 4 mM Tos-Gly-Pro-Arg-pNA-AcOH (Pefachrome® TH) and 100 µl of 5 µg/ml prothrombin activator from Notechis scutatus scutatus venom after the 8 minutes at 37° C. and the extinction variation is measured at 405 nm (Table 9). All the reagents were dissolved in 50 mM Hepes, 15 mM EDTA at pH 7.5. Measurements are taken in the presence and absence of APC. A ratio is again made from the extinction variation per minute without APC (−APC) and with APC (+APC).

The conversion of the chromogenic substrate is more strongly reduced in normal plasma in the presence of APC, as in this case normal FV is decomposed by APC and thus less thrombin is formed that splits off the chromogenic substrate. Consequently, the extinction variation per minute in normal plasma in the presence of APC is lower than in the presence of APC resistance.

The obtained results show that the chromogenic determination of APC resistance is also possible according to the invention and that in each case normal plasmas can be distinguished from heterozygous plasmas. In this example too, the addition of calcium ions is unnecessary.

TABLE 9

| | Normal plasma | | Heterozygous FV Leiden | |
|---|---|---|---|---|
| | +APC | −APC | +APC | −APC |
| Δ E/min | 0.036 | 0.115 | 0.105 | 0.183 |
| Ratio (−APC/+APC) | 3.18 | | 1.74 | |

EXAMPLE 9

Influence of Heparin on the Test System

The clotting time was determined with a coagulometer KC4 micro (Amelung, Lemgo, Germany). 40 µl of FV-deficient plasma (with or without polybrene), 10 µl of plasma sample and 50 µl of 2 U/ml Protac®, 1 U/ml of RVV-V and 0.1 mg/ml of cephalin were incubated for 20 minutes at 37° C. Clotting was triggered off by the addition of 50 µl of 5 µg/ml prothrombin activator from Notechis scutatus scutatus venom in 15 mM EDTA. All the reagents were dissolved in 50 mM Hepes, pH 7.5. The clotting time is determined in the presence and absence of Protac®. A ratio is obtained from the clotting time with Protac® and without Protac® (Table 10).

The results show that heparin in therapeutic concentrations in the presented test has no influence on the ratio. The addition of polybrene in the FV-deficient plasma does neither influence the ratio, but the clotting times are prolonged thereby.

TABLE 10

Plasma samples without heparin

| Plasma probe | FV-deficient plasma without heparin antagonist | | | FV-deficient plasma with heparin antagonist (Chromogenix ®) | | |
|---|---|---|---|---|---|---|
| | + Protac | − Protac | Ratio | + Protac | − Protac | Ratio |
| Normal plasma | 127.0 | 56.4 | 2.25 | 185.4 | 80.9 | 2.29 |
| Heterozygous FV defect | | | | 70.6 | 65.9 | 1.07 |
| Heterozygous FV defect | | | | 60.5 | 59.4 | 1.02 |
| Heterozygous FV delect | | | | 81.2 | 69.8 | 1.16 |
| Heterozygous FV def ect | | | | 103.4 | 78.6 | 1.32 |
| Heterozygous FV detect | | | | 124.9 | 94.5 | 1.32 |
| Heterozygous FV defect | | | | 92.8 | 69.9 | 1.65 |

Heparinized plasma: (0.5 or 1.0 Ul heparin/ml plasma sample).

| Plasma sample | FV-deficient plasma without heparin antagonist | | | FV-deficient plasma with heparin antagonist | | |
|---|---|---|---|---|---|---|
| | + Protac | − Protac | Ratio | + Protac | − Protac | Ratio |
| Heterozygous FV defect | | | | | | |
| 0.5 Ul heparin | 70.3 | 55.8 | 1.26 | 84.9 | 66.8 | 1.27 |
| 1.0 Ul heparin | 70.9 | 56.6 | 1.25 | 102.2 | 73.0 | 1.40 |

TABLE 10-continued

| Heterozygous FV defect | | | | | | |
|---|---|---|---|---|---|---|
| 0.5 Ul heparin | 88.1 | 62.2 | 1.42 | 113.7 | 83.9 | 1.36 |
| 1.0 Ul heparin | 86.8 | 62.2 | 1.40 | 119.3 | 83.0 | 1.44 |
| Normal | | | | | | |
| 0.5 Ul heparin | 170.4 | 61.6 | 2.77 | 206.3 | 84.2 | 2.45 |
| 1.0 Ul heparin | 179.0 | 62.4 | 2.87 | 206.3 | 92.1 | 2.24 |

What is claimed is:

1. A method for the qualitative detection and/or quantitative determination of disorders in the protein C system, comprising incubating a plasma sample with a protein C activator and/or APC, triggering off the coagulation by the addition of a calcium-independent prothrombin activator without addition of calcium ions to the test mixture, measuring the clotting time, comparing the latter with the clotting time with or without protein C activator and/or APC of a reference plasma sample and detecting the disturbance in the protein C system therefrom.

2. A method according to claim 1, wherein the reference plasma is a normal plasma.

3. A method according to claim 1, wherein the reference plasma is a part of the plasma sample to be investigated without addition of a protein C activator and/or APC.

4. A method according to claim 1, wherein the disorder in the protein C system is detected by forming a quotient with the clotting time of the plasma sample and the reference plasma.

5. A method according to one of the claims 1–4, wherein the measurement is carried out with synthetic chromogenic, fluorogenic or amperogenic substrates.

6. A method according to claim 1, wherein the plasma sample is pre-treated with citrate, oxalate or EDTA.

7. A method according to claim 1, wherein the protein C activator is a venom or at least a venom fraction from the snakes Agkistrodon contortrix and its subspecies, Agkistrodon piscivorus and its subspecies, Agkistrodon bilineatus and its subspecies and/or Agkistrodon halys and its subspecies.

8. A method according to claim 1, wherein the protein C activator is obtained from Agkistrodon contortrix contortrix.

9. A method according to claim 1, wherein the prothrombin activator is a snake venom with calcium-independent prothrombin activator activity in the form of crude venom or a purified crude venom fraction or a calcium-independent prothrombin activator from microorganisms with natural or recombinant genomes.

10. A method according to claim 9, wherein the snake venom with calcium-independent prothrombin activator activity is a venom from an Elapidae species.

11. A method according to claim 1, further comprising adding to the test mixture a phospholipid, a chelating agent, or a chelating agent analogue, a deficient plasma, protein C, protein S, factor VIII, a factor V activator and/or a heparin antagonist.

12. A method according to claim 11, wherein the deficient plasma is used in quantities of 99% to 1% up to 50% to 50% in relation to the plasma sample.

13. A method according to claim 11, wherein the factor V activator is RVV-V from Vipera russelli.

14. A method according to claim 11, wherein the heparin antagonist is hexadimethrine bromide, protamine sulfate or a heparin-splitting enzyme.

15. A method according to claim 11, wherein the chelating agent is citrate, oxalate, EGTA and/or EDTA.

16. A method according to claim 1, wherein said disorder in the protein C system is due to the increased stability of activated blood clotting factor V to decomposition by activated protein C.

17. A test kit for the qualitative detection and/or quantitative determination of disorders of the protein C system, comprising APC or a protein C activator and a calcium-independent prothrombin activator but no calcium ions.

18. A test kit according to claim 17, wherein said disorder of the protein C system is due to the increased stability of activated blood clotting factor V to decomposition by activated protein C.

19. A test kit according to claim 17 or 18, further comprising a factor V activator.

20. A test kit according to claim 17 or 18, further comprising a phospholipid, a factor V-deficient plasma, a Ca-complexing agent and, optionally, one or more reference plasmas.

21. A method according to claim 10, wherein the Elapidae species is Notechis scutatus scutatus, Notechis ater niger, Notechis ater humphreysi, Notechis ater serventyi, Notechis flinders, Notechis occidentalis, Tropidechis carinatus, Cryptophis nigrescens, Hoplocephalus stephensii and/or Pseudechis porphyriacus.

22. A method according to claim 11 or 12, wherein the deficient plasma is a factor V-, protein C-, or protein S-deficient plasma.

23. A method according to claim 16, wherein said disorder is FV Leiden.

24. A test kit according to claim 18, wherein said disorder is FV Leiden.

25. A test kit according to claim 19, wherein the protein C activator is obtained from Agkistrodon contortrix contortrix.

26. A test kit according to claim 20, wherein the Ca-complexing agent is EDTA.

* * * * *